(12) United States Patent
Silva et al.

(10) Patent No.: US 8,062,516 B2
(45) Date of Patent: Nov. 22, 2011

(54) LOW THERMAL MASS, ADJUSTABLE LOCKING GC NUT

(75) Inventors: Doug Silva, Lemoore, CA (US); Jim Archer, Sutter Creek, CA (US); Sky Countryman, Huntington Beach, CA (US); Kory Kelly, Carson, CA (US)

(73) Assignee: Phenomenex, Inc., Torance, CA (US)

( * ) Notice: Subject to any disclaimer, the term of this patent is extended or adjusted under 35 U.S.C. 154(b) by 804 days.

(21) Appl. No.: 12/170,145

(22) Filed: Jul. 9, 2008

(65) Prior Publication Data

US 2010/0005855 A1     Jan. 14, 2010

(51) Int. Cl.
*B01D 15/14* (2006.01)
*G01N 30/02* (2006.01)
*B01D 53/02* (2006.01)

(52) U.S. Cl. .................... 210/198.2; 73/23.35; 95/82

(58) Field of Classification Search ............... 210/198.2; 73/23.35, 23.39, 61.52, 61.53; 95/82; 422/70
See application file for complete search history.

(56) References Cited

U.S. PATENT DOCUMENTS

| | | | | |
|---|---|---|---|---|
| 4,966,550 A * | 10/1990 | Privat | ............................. | 433/25 |
| 5,938,919 A * | 8/1999 | Najafabadi | ................ | 210/198.2 |
| 6,095,572 A * | 8/2000 | Ford et al. | ..................... | 285/361 |
| 6,361,687 B1 * | 3/2002 | Ford et al. | ................... | 210/198.2 |
| 7,507,336 B2 * | 3/2009 | Quimby et al. | ............ | 210/198.2 |

OTHER PUBLICATIONS

Agilent, Agilent Technologies, Column nut for GC capillaries 2/pk, http://chem.agilent.com/en-US/Store/_layouts/Agilent/Commerce/ProductDetail.aspx?productID=5181-8830, accessed online Mar. 12, 2009.

Alltech,Discovery Sciences, GC Accessories Injector; Deactivated Injection Liners, Deactivated SGE FocusLiners, Accessories for Agilent and Varian Capillary Sytems, pp. 286-388, www.discoverysciences.com/uploadedFiles/Site_for_Catalog_2008/gc/GC_Accessories/Injection_Liners_and_Accessories, (2008) publication; accessed online Mar. 12, 2008.

Sigma-Aldrich, 24833-U Supelco Column Nut, http://www.sigmaaldrich.com/catalog/ProductDetail.do?N4=24833U%7CSUPELCO&N5=SEARCH_CONCAT_PNO%7CBRAND_KEY%F=SPEC, accessed online Mar. 12, 2009.

Sigma-Aldrich, 22509 Supleco Ferrule Nut Adapter, http://www.sigmaaldrich.com/catalog/ProductDelail.do?N4=22509%7CSUPELCO&N5=SEARCH_CONCAT_PNO%7CBRAND_KEY&F=SPEC, accessed online Mar. 12, 2009.

Restek, Capillary Installation Gauge for Agilent 5973/5975 MS, www.restek.com/restek/prod/4012.asp, accessed online Mar. 12, 2009.

Restek, Capillary Installation Gauge for Agilent GCs, www.restek.com/restek/prod/3014.asp, accessed online Mar. 12, 2009.

Restek, Capillary installation Gauge for Shimadzu 17A, 2010, & 2014 GCs, www.restek.com/restek/prod/7199.asp, accessed online Mar. 12, 2009.

Restek, Capillary Installation Gauge for TRACE & Focus SSL, www.restek.com/restek/prod/6665.asp, accessed online Mar. 12, 2009.

Restek, Capillary Instalation Gauge for Varian GCs, www.restek.com/restek/prod/8409.asp, accessed online Mar. 12, 2009.

* cited by examiner

*Primary Examiner* — Lisa Caputo
*Assistant Examiner* — Punam Roy
(74) *Attorney, Agent, or Firm* — Stetina Brunda Garred & Brucker; Lowell Anderson (57) ABSTRACT

A connector for fastening a gas chromatography capillary column to chromatography equipment includes a securing nut and ferrule on a first portion of the connector for releasably holding the capillary column in a position relative to a second portion of the connector. The first portion rotates relative to the first portion and translates a limited amount relative to the first portion. A pin on the first portion extending into an annular groove around a circumference of the first portion may allow this rotation and limited translation. The second portion has a threaded end adapted to screw into the chromatography equipment with the first portion remaining relatively rotation free as the second portion is screwed into place.

20 Claims, 4 Drawing Sheets

LOW THERMAL MASS, ADJUSTABLE LOCKING GC NUT

BACKGROUND

Gas chromatography equipment requires connecting very thin capillary tubes to equipment, and often disconnecting and reconnecting the tubes during operations. Typically the installer passes the column through a threaded fastener containing a ferrule with the fastener screwed into/onto a mating inlet of the equipment. If the column installation depth is too long or too short, chromatographic problems may result. It is also difficult sometimes to reach the installation inlets, and if the column must be changed during use or immediately after use, the column and fastener are hot and the user must wait a long time until they cool. Because the installation port of the GC analyzers are hot after use, it is easy to burn fingers when connecting the columns, and in the rush to install hot parts threads are often cross-threaded, leading to further installation delays and damage to equipment.

After use, the oven needs to cool down to a temperature comfortable to the user's touch so the nut that holds the column in place can be loosened by hand. It can take up to 20 minutes to cool the parts. After detaching the nut, a new column is inserted through the nut and ferrule and positioned into the injector at a specified depth. The nut and ferrule are then finger-tightened and given an extra half turn with a wrench until the column is secured. If the oven is not cooled down enough, the user's fingers will be burned when they touch the capillary nut. Thermal installation gloves help prevent burns, but gloves fray or stretch and impair the sensitivity of tightening.

Setting an appropriate column depth is also important since the depth affects reproducibility of the results. The columns are often marked with correction fluid to denote the correct installation depth, but the correction fluids are messy, they smear and they burn in the oven.

An improved installation mechanism is needed.

BRIEF SUMMARY

A fastening assembly is provided which has an installation hub and a second securing nut. The hub is about ⅛ inch below or upstream of the optional wrenching surface of the main body, allowing the user's fingers to stay well below and to the outside of a mating inlet of the equipment which gets very hot during use. The hub's low thermal mass makes it more comfortable to install or manually remove without waiting for the inlet/detector to cool. The hub also acts as a tightening device so the GC column can be hand-tightened into place with a slight mechanical advantage over the traditional, smaller nut, thus eliminating the need for a wrench.

Upstream of the hub is a second nut with a compression ferrule that holds the column at a constant length during the installation process. An installation gauge can help set a proper and constant installation depth to assure the accuracy and reproducibility of the analysis.

The capillary GC column is threaded through a securing nut, and a main body which contains a securing base on the upstream side of the base. A lower or upstream ferrule is placed between the securing base and the main body and an upper or downstream ferrule is on the downstream side of the main body. Both ferrules point with their tapered end toward the column's end which extends through and past the main body. About 1 cm is trimmed from the end of the capillary using a scoring wafer or scoring pen to remove any graphite introduced inside the column from passing through the ferrules or main body. The securing nut is tightened to the securing base to compress the ferrule against the securing base and is tightened until the column can slide through the lower ferrules but with resistance.

If the column installation depth is known for the particular equipment, usually a GC injector/detector, then the column installation depth is adjusted to extend beyond the main body a distance specified according to the analytical equipment manufacturer's recommendations, and this adjustment is done while the securing body is apart and separate from the analytical equipment. When the desired length of the column extends beyond the main body the securing nut is tightened against the securing base so the column will not slide relative to the securing base. The securing base can rotate within the main body and slide slightly (about 1 mm) relative to the main body, along the column axis. The main body is then connected to the equipment.

The main body is rotated, typically threaded into, a standard mating aperture on the inlet of the gas chromatography inlet or detector to fasten the column to the equipment. The securing base is allowed to freely rotate relative to the rotating main body during this rotational fastening. As the main body is fastened to the equipment the upper ferrule is seated to the equipment and restrains movement and rotation of the column.

To check and see if the upper ferrule is seated or swaged properly the securing base is urged gently upwards or downstream towards the equipment. If movement is noticed the securing base is pulled downward as far as it will go and the main body is retightened, with the securing base being urged upwards to recheck the seating. The column is ready to be leak checked when the securing base is no longer freely movable in and out of the main body.

The interface between the securing base and the main body is checked for leaks, as is the location where the column exits the securing base and also the location between the lower securing nut and the securing base. The column is then installed and ready for use.

There is thus advantageously provided a first embodiment of a connector for connecting a gas chromatography capillary column to chromatography equipment, where the equipment has a connection for releasably connecting to capillary columns. The connector has a longitudinal axis along which the capillary column extends during use. The connector includes a securing body, a securing nut and a main body. The securing body has an upstream and downstream end with a ferrule recess in the upstream end configured to receive an upstream ferrule. The securing body also has an annular recess extending around an exterior circumference of the downstream end of the securing body. The securing nut holds the upstream ferrule in the securing body. The main body has an upstream and downstream end with a recess in the upstream end of the main body that is sized to slidably and rotatably receive the downstream end of the securing body. The downstream end of the main body is configured to releasably connect with the releasable connection on the equipment. The downstream end of the main body has a ferrule recess into which a downstream ferrule can be placed during use. The main body has a part extending into the annular recess to limit motion of the securing body relative to the main body in at least one direction along the longitudinal axis, with the longitudinal axis extending through the securing nut, upstream ferrule, securing body and main body.

In further variations of this first embodiment, a finger gripping surface is connected to the main body and located outward from the longitudinal axis a distance sufficient to allow manual tightening of the connection with the chromatography equipment sufficient for use of the equipment and without using wrenches. The finger gripping surface may be on the outer periphery of a flange, where the flange having a plurality of holes there through. The securing nut may be threaded onto the upstream end of the securing body. The connection with the equipment may comprise a threaded connection and the main body may have external threads on the downstream end configured to mate with the threaded connection on the equipment. A wrenching surface is optionally provided on an exterior surface of the main body to allow one to mechanically tighten the main body to the connection on the equipment. A downstream ferrule can be seated in the recess in the downstream end of the main body during use. The annular recess may have an outwardly extending wall on opposing sides of the recess, with one wall abutting a shoulder on the main body to limit movement of the securing body along the longitudinal axis relative to the main body.

In a further embodiment there is advantageously provided a connector for connecting a gas chromatography capillary column to chromatography equipment having a releasable connection to connect the column to the equipment, where the capillary column and connector have a common longitudinal axis. The connector includes first means on a first portion of the connector for releasably holding the capillary column in a position relative to a second portion of the connector. The connector also includes means for adjusting the axial position of the first means relative to the second portion of the connector, and means for allowing the first means to rotate relative to the second portion of the connector as the connector is fastened to the equipment during use of the connector. The connector also includes means for connecting the second portion to the equipment during use of the connector.

The first means may include a threaded securing nut the tightening of which causes a ferrule to clamp against the column and the loosening of which allows the column to slide relative to the ferrule. The means for allowing the first means to rotate may include a pin on the second portion extending into a recess on the first portion. The means for allowing the first means to rotate may include a pin on the second portion extending into a recess on the first portion. The connector may further include an enlarged gripping means for manually tightening and cooling the connector. The connection on the chromatography equipment advantageously includes a threaded connection and the means for connecting comprises a threaded end on the connector configured to threadingly engage the threaded connection on the chromatography equipment.

There is also advantageously provided a method for using a connector to connect a gas chromatography capillary column to chromatography equipment having a releasable connection, where the capillary column and connector have a common longitudinal axis. The method may include passing the capillary column through a securing nut and first ferrule, where the securing nut threadingly engages the first body and the first ferrule held in a recess in the first body. The capillary column is passed through a second body main body and second ferrule so a distal end of the capillary column extends beyond the second ferrule. The first body rotates within the second body and relative to the second body. The first body is connected to the second body to allow the first body to slide within and relative to the second body a short distance to adjust the capillary column length but is prevented from being withdrawn from the second body by a restraint. The method further includes cutting off a portion of the distal end and tightening the first ferrule to limit motion of the capillary column relative to the first body before or after the cutting step. The method also includes rotating the second body relative to the first body to fasten the connector to the equipment while allowing the first body and second bodies to translate along the longitudinal axis.

In further variations, the method also includes translating the first body relative to the second body along the longitudinal axis to move the distal end of the capillary column away from the equipment. The method may also include rotating the second body relative to the first body to move the distal end of the capillary column toward the equipment. The relative rotation may be achieved by having a portion of the second body extend into an annular groove extending around a circumference of the first body. The first body may be prevented from being withdrawn from the second body by having a portion of the second body extending to an annular groove extending around a circumference of the first body.

The method may also include adjusting the distance by which the distal end of the capillary column extends beyond the second portion to a predetermined distance after cutting off a portion of the distal end. The adjusting may include the intermediate steps of rotating the second body relative to the first body to fasten the connector to a base having a connection like that of the equipment followed by extending the cut distal end through a hole in a base and along a scale until the distal end reaches a desired location on the scale, and then performing the tightening step of the originally described method. The rotating step may be achieved by manually rotating an enlarged hub on the second body to achieve a connection sufficient for use.

An apparatus is also optionally provided for adjusting the length of a gas capillary column. The scale has a base with a releasable connection just like the connection used to connect gas capillary columns to chromatographic analyzers. The base has a hole extending therethrough and aligned with a longitudinal axis of the connection so that a capillary column connected to the base can pass through the hole during use. A scale extends from the base and along the longitudinal axis opposite the connection. The scale has printed indicia thereon indicating the length by which a distal end of the capillary column extends beyond a predetermined location. The printed indicia is preferably fractions of an inch or centimeter, but could be length indications for specific types of applications or equipment. The releasable connection may include a female threaded coupling. The measurement device described here (but not the connection to the GC column) is commercially available from several GC manufacturers/vendors.

BRIEF DESCRIPTION OF THE DRAWINGS

These and other features and advantages of the various embodiments disclosed herein will be better understood with respect to the following description and drawings, in which like numbers to like parts throughout, and in which:

FIG. 3b shows a sectional view of the main body of FIG. 3a taken along section 3b-3b of FIG. 3a;

DETAILED DESCRIPTION

Referring to FIGS. 1-7 and 12, a tubular gas chromatography (GC) column 10 is releasably connected to a sample injector 11 at one end and to a detector 12 at the other end of the column, both using a connector assembly 14. The GC column 10 is typically placed inside an oven 13, so the connector assembly 14 is hot. The analytical equipment 15 typically includes a GC analyzer that includes the injector 11, detector 12, column 10 and oven 13, with the column and connector 14 typically located inside the oven. The GC analyzer has a threaded mating inlet 16 into which an end of the column 10 fits. As used herein, upstream and downstream refer to the flow direction in the GC column from the injector 11 toward the detector 13, with a downstream part being closer to the detector 12 along the flow path of the capillary tube than is an upstream part, and an upstream part being farther from the detector 12 along the flow path than a downstream part. A downstream flow or direction is toward the detector 12, and an upstream flow or direction is away from the detector 12. These connectors and equipment are usually arranged so the connectors are oriented as in FIGS. 4 and 7, with upstream being down, and downstream being up as shown in those figures. Thus, upper and lower are with respect to these directions and FIGS. 4 and 7.

Referring to FIGS. 1-7 and 12, the GC column typically comprises a long, thin capillary tube of silica having a distal end 17 connected to the equipment 15 so that gases passing through the tube 10 enter the detector 12. The connector assembly 14 contains a securing nut 18, lower ferrule 20, securing base 22, main body 24 and upper ferrule 26, with the GC column passing sequentially through these parts, namely the securing nut 18, lower ferrule 20, securing base 22, main body 24 and upper ferrule 26, respectively. The securing nut may be a cup-shaped part with a wrenching or hand gripping surface 28 on the exterior for easy tightening by hand, with the inside 30 configured to receive the lower ferrule 20 and a hole 32 in the otherwise closed end through which the GC column passes. The depicted configuration has a rounded exterior with opposing flattened sides to form the wrenching surface 28, but other exterior configurations could be used, such as a knurled surface 28 for hand tightening. The interior 30 opens downstream toward GC column end 17 and may be threaded. The lower and upper ferrules 20, 26, respectively, are typically of graphite, vespel/graphite, or other malleable, temperature resistant materials and cylindrical with a tapered surface on one end. Preferably both ferrules 20, 26 preferably point with their tapered side toward the column distal end 17. A hole extends through the ferrules 20, 26 through which the GC column passes.

The securing base 22 has a male end projecting upstream and threaded to engage with the threads on the interior 30 of the securing nut. The securing base 22 has a tubular downstream end 34 (FIG. 7) extending downstream toward the detector 12 with an annular groove or recess 36 (FIG. 7) extending around an outer periphery of the securing base 22, which recess may be adjacent downstream end 34. The upstream end of the securing base 22 preferably has wrenching surface 35, which may comprise a plurality of opposing flats or a knurled surface.

The main body 24 has a tubular body 40 with outwardly extending hub 42 preferably having a knurled exterior surface. A cylindrical internal passage 44 extends through the main body 24 with an inwardly stepped shoulder 46 (FIG. 7) or other partial obstruction located toward the downstream end 48 of the body 40. Advantageously, the end 48 is about an inch from the hub 42 to help distance a user's fingers gripping the hub 42 from the hot connection with the equipment 15. The upstream end of the passage 44 is sized slightly larger than the downstream end 34 of the securing base so the end 34 slides (and rotates) within the passage 44 until the end 34 abuts shoulder 46. A fastener 38 such as a pin, set screw or set pin extends through main body 24 and fits into recess 36 in the securing base when end 34 abuts shoulder 46. The recess 36 allows limited axial movement of securing base 22 along the GC axis through the securing base 22. About 0.05 inches of travel is believed suitable but the amount of travel can vary. Optionally, a plurality of holes 50 can be placed in the outwardly extending flange portion of hub 42. Ten such holes 50 are shown (FIGS. 5-6), but the number can vary. The downstream end 48 of main body 24 has threads configured to mate with the mating inlet 16 of the equipment 15. A wrenching surface 52 can optionally be provided on the exterior surface of body 40.

Figure 1:
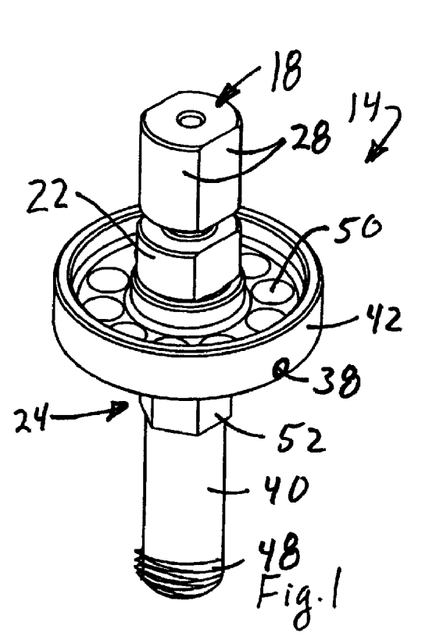
FIG. 1 shows a perspective view looking downstream onto the connector assembly of this invention.
Figure 2:
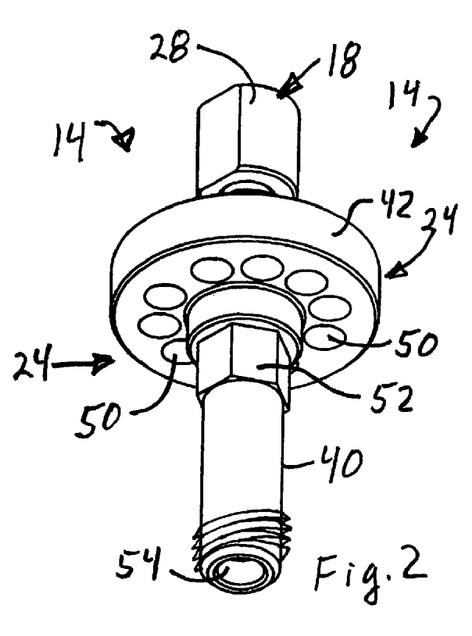
FIG. 2 shows a perspective view looking upstream onto the connector assembly of FIG. 1.
Figure 3A:
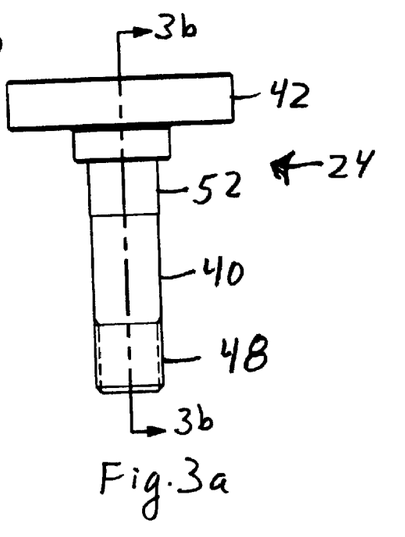
FIG. 3a shows a side plan view of a main body used in the assembly of FIG. 1.
Figure 3B:
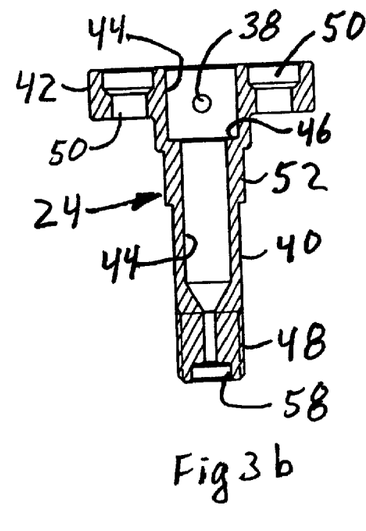
Figures 4, 5, 6, 7:
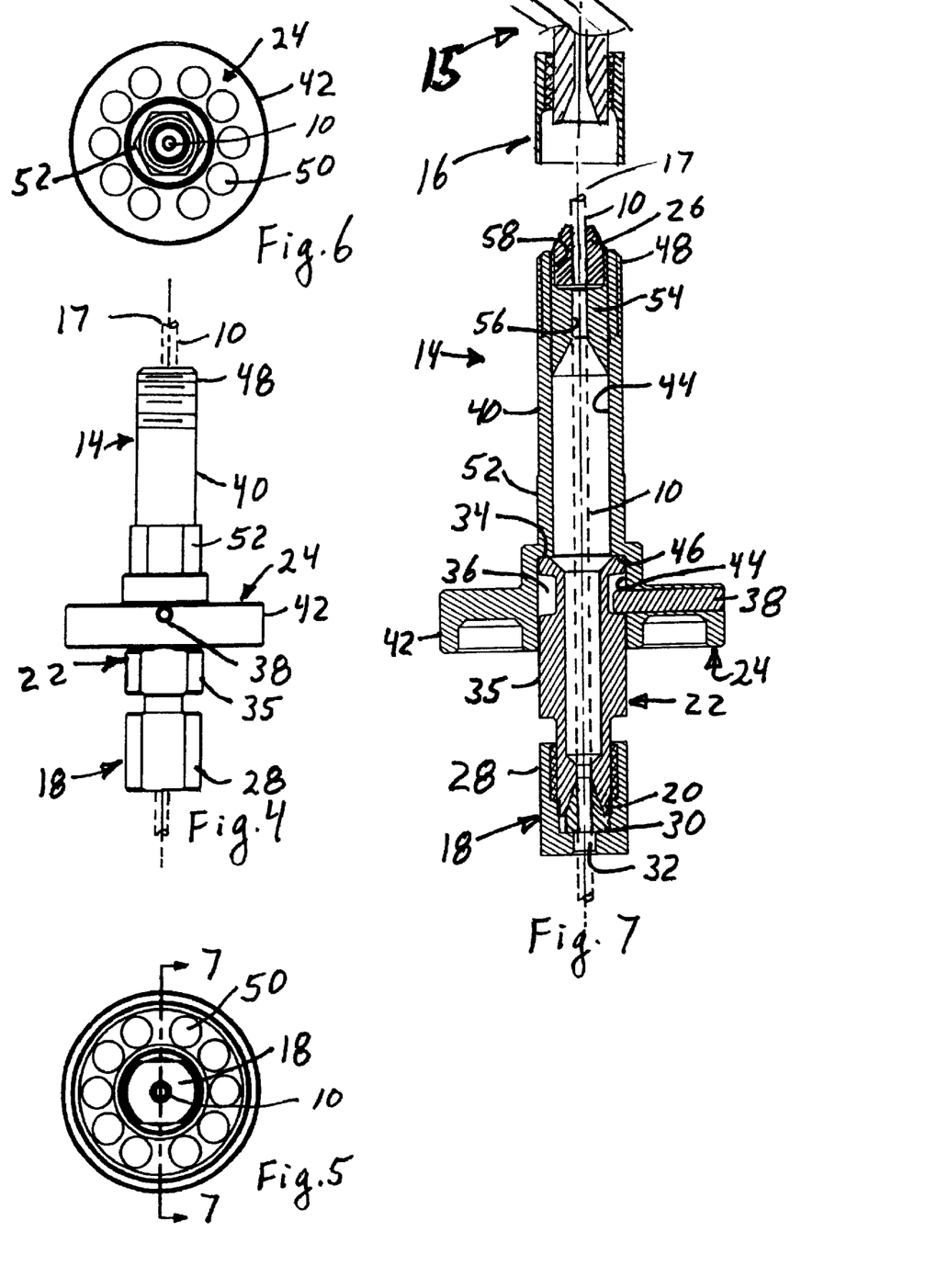
FIG. 4 shows a side plan view of the connector assembly of FIG. 1.
FIG. 5 shows a top plan view of the connector assembly of FIG. 3.
FIG. 6 shows a bottom plan view of the connector assembly of FIG. 3.
FIG. 7 shows a cross sectional view taken along 7-7 of FIG. 5.
Figure 8:
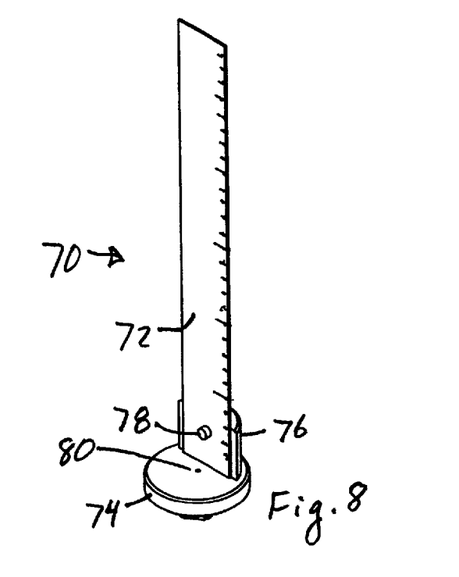
FIG. 8 is a perspective view of an installation gauge especially useful with the connector assembly of FIG. 1.
Figure 9:
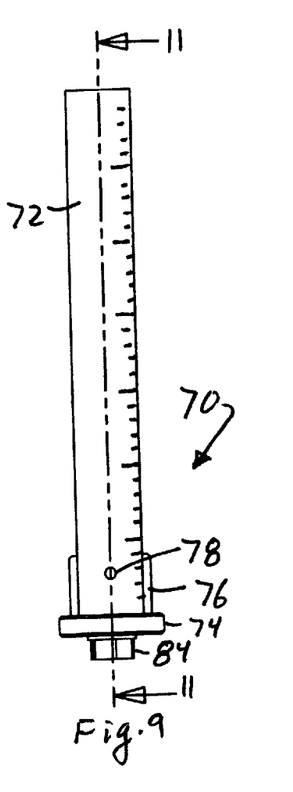
FIG. 9 is a front plan view of the gauge of FIG. 8.
Figure 10:
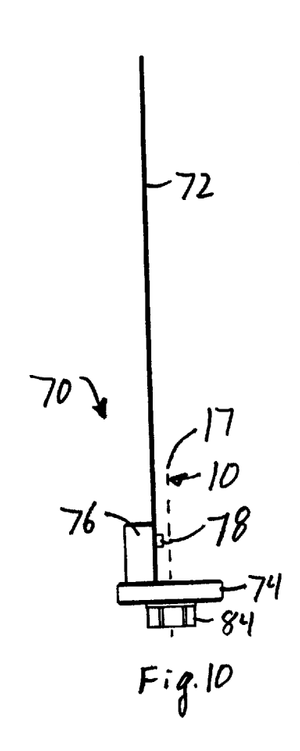
FIG. 10 is a left side plan view of the gauge of FIG. 9, with the opposing side view being the mirror image thereof.
Figure 11:
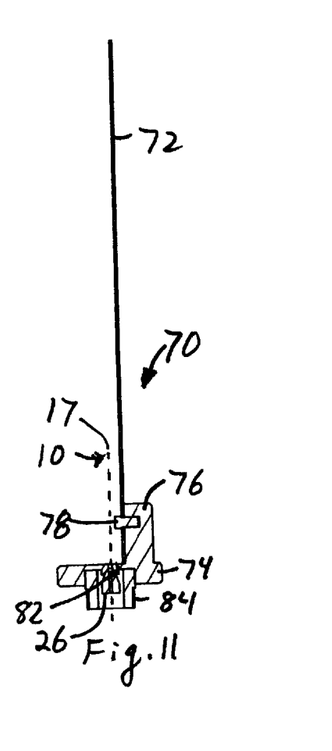
FIG. 11 is a sectional view taken along 11-11 of FIG. 9.
Figure 12:
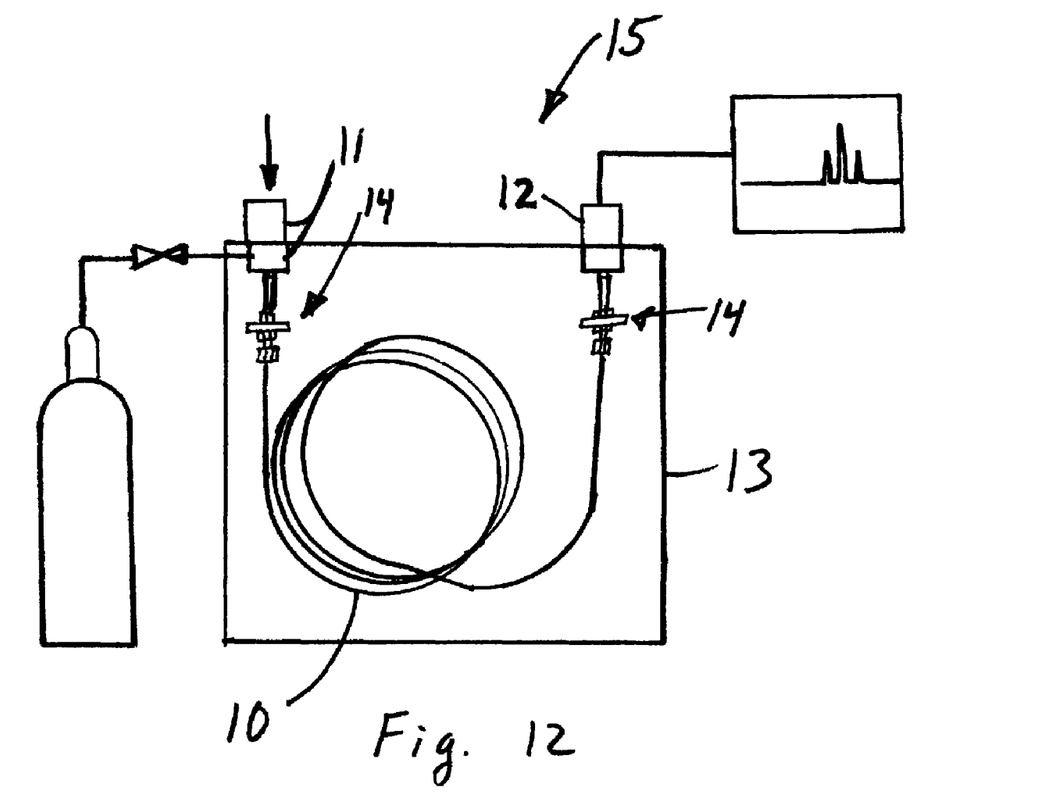
FIG. 12 is a schematic view of a gas chromatography column connected to equipment through a connector assembly

The depicted configuration can be machined, formed or cast into a solid tubular part of a single piece of material. Alternatively, a plug 54 (FIG. 7) is optionally placed into the downstream end 48 of the main body 24. The plug 54 has a hole 56 sized to GC column 10 passes therethrough at the center of the tubular body 40. A cup-shaped recess 58 is formed in the downstream end of the plug 54 and faces downstream toward detector 12 to receive upper or downstream ferrule 26 (FIG. 7).

In use, the GC column 10 passes through securing nut 18, lower ferrule 20, securing base 22, main body 24, plug 54 and upper ferrule 26. Tightening the threaded connection between the securing nut 18 and securing base 22 allows the lower ferrule to adjustably grab the GC column 10 and hold it. The sliding and rotating of the securing base 22 relative to the main body allows rotational and axial movement of the GC column 10 between the securing base 22 and main body 24. That allows the securing nut and securing body to grip the GC column 10 and allow it to move while the threaded end 48 of the main body is rotatably screwed into the mating connector 16 of the GC equipment 15. The movement allows rotation and limited axial movement to more accurately engage distal end 17 of the GC column with the equipment 15.

In use, the GC column 10 is threaded through securing nut 18, lower ferrule 20, securing base 22, main body 24, plug 54 and upper ferrule 26. Again, both ferrules 20, 26 point with their tapered end toward the column's end 17 which extends through and past the main body 24. About 1 cm is trimmed from the end of the capillary column 10 using a scoring wafer or scoring pen to remove any graphite introduced inside the column 10 from passing through the ferrules 20, 26, main body 24 or other parts. The securing nut 18 is then tightened to the securing base 22 to compress the lower ferrule 20 against the securing base and is tightened until the column 10 can slide through the lower ferrule but with resistance.

If the installation depth of the GC column 10 is known for the particular equipment 15, then the column installation depth is adjusted to extend beyond the main body a distance specified according to the analytical equipment manufacturer's recommendations, and this adjustment is done while the securing body is apart and separate from the analytical equipment. When the desired length of the column extends beyond the main body the securing nut 18 is tightened against the securing base 22 to fix the length of column extending beyond end 48 of main body 24, so the column 10 will not slide axially relative to the securing base 22.

The securing base 22 can rotate within the main body 24 and slide slightly (about 1 mm) relative to the main body, along the column axis. The fastener, such as set pin 38 and recess 36 allow rotation and can define some or all of the axial movement, although the end 34 abutting shoulder 46 can also limit the axial movement in the upstream direction toward detector 12. This allows the main body 24 to be screwed into the equipment 15 without twisting the column 10, and it allows for minor length adjustment.

The main body 24 is then connected to the equipment 15, but the connection is typically 1 inside oven 13, or affixed to oven 13 so the connection becomes hot. The main body 24 is rotated, typically threaded into/onto, the mating fitting/inlet 16 on the inlet of the gas chromatography sample inlet 11 or detector 12 or other equipment 15 to connect the column 10 to the equipment. The securing base 22 is allowed to freely rotate relative to the main body 24 as the main body is screwed into the equipment 15. As the main body 24 is fastened to the equipment 15 the upper ferrule 26 is seated to the equipment 15 and also grips the column 10 to restrain movement and rotation of the column. When installed, the upper and lower ferrules 20, 26 grip column 10, and the connector assembly 16 is of fixed configuration and does not rotate or translate.

To check and see if the upper ferrule 26 is seated or swaged properly against the column 10, the securing base 22 is urged gently upwards or downstream towards the equipment 15. If movement is noticed the securing base 22 is pulled upstream as far as it will go (set pin 38 and groove 36 limit this movement) and the main body 24 is retightened. The check and retighten procedure is repeated until the column is fully seated in the equipment 15. The column 10 is ready to be leak checked when the securing base 22 is no longer freely movable in and out of the main body 24.

The interface between the securing base 22 and the main body 24 is then checked for leaks, as is the location where the column exits the securing base and also the location between the lower securing nut and the securing base. The column is then installed and ready for use. The wrenching surfaces 35, 52 allow the use of tools if desired, while also allowing manual manipulation. But the hub 42 is larger in diameter than the traditional fastening nut, preferably with a diameter of about one inch, and that larger diameter allows greater tightening force by using fingers alone, and can allow installation without the use of tools.

To disconnect the GC column, the oven 13 is programmed to ambient conditions and the oven is allowed to cool. Because the column 10 and connector assembly 14 get very hot during use, the system gas flows are turned off. After the connector assembly 14 is cooled enough, the hub 42 is manually manipulated so the main body 24 and end 48 of tube 40 are unscrewed from the equipment 15. The column 10 can then be removed by loosening the securing nut 18 and withdrawing the column 10 for reuse. Alternatively, another connector assembly 14 can be previously installed onto another column 10 for immediate reconnection.

The ability to adjust the extension of the column 10 by using the connector assembly 14 and to hold that adjusted configuration can save a lot of time. The ease of manipulation while the thin tube is inserted into the mating connector 16 of the GC equipment is also very useful. The larger diameter hub provides for easy gripping, while the securing nut 18 and securing base 22 hold the GC column in position relative to the threaded end 48 of the main body. The hub 42 and the longer upstream tube 40 allows easier insertion and manipulation of the GC column 10, and the connector assembly 14 allows rotation without twisting and breaking the column during the rotation needed to connect to the equipment. The ability to axially move the GC column relative to the partially engaged main body 24 allows fine adjustment to more securely and safely seat the thin GC column into the equipment 15 without damage. Moreover, the larger main body 24 provides a larger heat conduction surface and radiating surface so the hub 42 cools faster. The GC column 10 and assembly 14 get hot during use, too hot to comfortably handle. The improved heat dissipation is believed to help the hub 42 cool faster so an operator can unfasten the main body 24 faster than with the prior art. The hub 42 can optionally be made of aluminum to further enhance cooling, and the holes 50 are believed to increase radiation area while increasing conduction to air passing through the holes.

The connector assembly 14 thus helps reduce the time waiting for the inlet or detector on the equipment 15 to cool before installing the column because the connector 14 is handled and distances the user's fingers from the inlet and other hot equipment. The elimination of the need to cool the injector and detector also reduces the time for the equipment 15 to heat back up to operating time and stabilize before resuming analysis. The cooler hub 14 also allows a user to use bare fingers rather than thermal insulating gloves and that allows for greater finger sensitivity on tightening the mating parts. The ability to pre-determine the length of the GC column 10 beyond the end 48 of the main body 24 allows for more accurate installation where the distance is predetermined and known. The adjustment of the length and the ability to secure that length with a compression system, eliminates the possibility for errors while ensuring proper seating and installation. The installation maintains the upper ferrule 26 away from the distal end 17 of the column 10 and in the cup 58 so the end 17 cannot slip into the ferrule during installation. The installation does not require correction fluid or a septum to ensure correct column installation depth.

Referring to FIGS. 8-11, an installation gauge 70 is preferably used to ensure the appropriate length of the column 10 in the connector assembly 14. The gauge 70 has a graduated scale 72 typically a flat ruler marked with appropriate dimensions such as mm or inches and fractions thereof to gauge the length of the column 10. The scale 72 is fastened to a base 74 that may be adapted to be held by the user's hand. The depicted base 74 has a circular disc about 2-3 cm in diameter and 0.5 cm thick, with a flange 76 extending upward from the disk at a right angle. The scale 72 is fastened to the flange 76. Various fastening mechanisms can be used, including adhesives, welding, or threaded fasteners. In the depicted embodiment a set pin 78 holds the scale 72 to the flange 76, with a square end of the scale resting against the upper surface of the base 74.

A hole 80 extends through the base 74, with the hole sized to allow capillary tube 10 to pass therethrough. The bottom of the base 84 is configured to resemble the mating inlet 16 on GC equipment 15, so there is a conical surface 82 surrounding hole 80 into which upper ferrule 26 fits during use of the gauge 70. The tapered surface 82 is surrounded by a female connector 84 with internal threads configured to threadingly engage threads on out outer surface of end 48. A wrenching or tightening surface 86 may be placed on the exterior of the connector 84.

In use, the column 10 is inserted through the connector assembly 14 as described earlier and the column 10 is cut leaving about 1 cm or more of the column extending beyond the upper ferrule 26. The column end 17 and end 48 are inserted into/onto the mating inlet of the equipment 84 and the column 10 through hole 80. The hub 42 is rotated and threaded into the female connector 84 until the upper ferrule 26 starts to compress. The length of the column is adjusted to the desired length, using the scale 72 to measure the desired insertion distance into the equipment 15. When the length of the column is adjusted then the connector 84 can be tightened to clamp the ferrule 26 against the column 10 and restrain movement of the column relative to the gauge 70. The securing nut 18 is then tightened so the lower ferrule 20 clamps the column 10 to restrain axial movement of the column 10 relative to the connector assembly 14, and this should be done with the securing base in the fully extended position to achieve the correct premeasured position and to allow for proper leak checking. This tightening of the nut 18 could be done without tightening the connector 84 on the gauge 70.

In short, the bottom of the gauge 70 simulates a connector with the equipment 15 and allows the length of column 10 to be visually adjusted outside of the equipment, at which time the desired column length is either marked or set by clamping the column 10 in the connector assembly 14 (via securing nut 18 and lower ferrule 20).

If the connector assembly 14 is not being used, the column can be marked at the base of the column nut to identify the correct depth after installation. The mark on the column allows correctly positioning the column relative to the equipment 14 before tightening the nut ¼ to ½ turn past finger tight.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A connector for connecting a gas chromatography capillary column to chromatography equipment, the equipment having a connection for releasably connecting to capillary columns, the connector having a longitudinal axis along which the capillary column extends during use, the connector comprising:
    a securing body having an upstream and downstream end with a ferrule recess in the upstream end configured to receive an upstream ferrule, the securing body having an annular recess extending around an exterior circumference of the downstream end;
    a securing nut holding the upstream ferrule in the securing body; and
    a main body having an upstream and downstream end with a recess in the upstream end of the main body being sized to slidably and rotatably receive the downstream end of the securing body and with the upstream end of the main body configured to releasably connect with the releasable connection on the equipment, the downstream end of the main body having a ferrule recess into which a downstream ferrule can be placed during use, the main body having a part extending into the annular recess to limit motion of the securing body relative to the main body in at least one direction along the longitudinal axis, with the longitudinal axis extending through the securing nut, upstream ferrule, securing body and main body.

2. The connector of claim 1, further comprising a finger gripping surface on the main body and located outward from the longitudinal axis a distance sufficient to allow manual tightening of the connection with the chromatography equipment sufficient for use of the equipment.

3. The connector of claim 1, further comprising a finger gripping surface on the outer periphery of a flange, the flange having a plurality of holes there through.

4. The connector of claim 1, wherein the securing nut is threaded onto the upstream end of the securing body.

5. The connector of claim 1, wherein the connection with the equipment comprises a threaded connection and the main body has external threads on the downstream end configured to mate with the threaded connection on the equipment.

6. The connector of claim 1, further comprising a wrenching surface on an exterior surface of the main body to allow mechanically tighten of the main body to the connection on the equipment.

7. The connector of claim 1, further comprising a downstream ferrule seated in the recess in the downstream end of the main body.

8. The connector of claim 1, wherein the annular recess has an outwardly extending wall on opposing sides of the recess, with one wall abutting a shoulder on the main body to limit movement of the securing body along the longitudinal axis relative to the main body.

9. A connector for connecting a gas chromatography capillary column to chromatography equipment having a releasable connection to connect the column to the equipment, the capillary column and connector having a common longitudinal axis, the connector comprising:
    first means on a first portion of the connector for releasably holding the capillary column in a position relative to a second portion of the connector;
    means for adjusting the axial position of the first means relative to the second portion of the connector;
    means for allowing the first means to rotate relative to the second portion of the connector as the connector is fastened to the equipment during use of the connector; and
    means for connecting the second portion to the equipment during use of the connector.

10. The connector of claim 9, wherein the first means comprises a threaded securing nut the tightening of which causes a ferrule to clamp against the column and the loosening of which allows the column to slide relative to the ferrule.

11. The connector of claim 9, wherein the means for allowing the first means to rotate comprises a pin on the second portion extending into a recess on the first portion.

12. The connector of claim 9, further comprising an enlarged gripping means for manually tightening and cooling the connector.

13. The connector of claim 9, wherein the connection on the chromatography equipment comprises a threaded connection and the means for connecting comprises a threaded end on the connector configured to threadingly engage the threaded connection on the chromatography equipment.

14. A method for using a connector to connect a gas chromatography capillary column to chromatography equipment having a releasable connection, the capillary column and connector having a common longitudinal axis, the method comprising:

passing the capillary column through a securing nut and first ferrule, the securing nut threadingly engaging the first body and the first ferrule held in a recess in the first body;

passing the capillary column through a second main body and second ferrule so a distal end of the capillary column extends beyond the second ferrule, the first body rotating within the second body and relative to the second body, the first body being connected to the second body to allow the first body to slide within and relative to the second body a short distance to adjust the capillary column length but being prevented from being withdrawn from the second body by a restraint;

cutting off a portion of the distal end;

tightening the first ferrule to limit motion of the capillary column relative to the first body before or after the cutting step;

rotating the second body relative to the first body to fasten the connector to the equipment while allowing the first body and second bodies to translate along the longitudinal axis.

15. The method of claim 14, further comprising translating the first body relative to the second body along the longitudinal axis to move the distal end of the capillary column away from the equipment.

16. The method of claim 15, further comprising rotating the second body relative to the first body to move the distal end of the capillary column toward the equipment.

17. The method of claim 14, wherein the relative rotation is achieved by having a portion of the second body extend into an annular groove extending around a circumference of the first body.

18. The method of claim 17, wherein the first body is prevented from being withdrawn from the second body by having a portion of the second body extending to an annular groove extending around a circumference of the first body.

19. The method of claim 14, further comprising adjusting the distance by which the distal end of the capillary column extends beyond the second portion to a predetermined distance after cutting off a portion of the distal end.

20. The method of claim 14, wherein the rotating step is achieved by manually rotating an enlarged hub on the second body to achieve a connection sufficient for use.

\* \* \* \* \*